US007279000B2

(12) United States Patent
Cartier et al.

(10) Patent No.: US 7,279,000 B2
(45) Date of Patent: Oct. 9, 2007

(54) PERMANENT BLOOD CLOT FILTER WITH CAPABILITY OF BEING RETRIEVED

(76) Inventors: William A. Cartier, 42 Perry Heights, Hampton, NY (US) 12832; Giorgio di Palma, 81 Sara-Jen Dr., Queensbury, NY (US) 12804; William M. Appling, 8291 State Route 40, Granville, NY (US) 12832

( * ) Notice: Subject to any disclaimer, the term of this patent is extended or adjusted under 35 U.S.C. 154(b) by 18 days.

(21) Appl. No.: 11/165,675

(22) Filed: Jun. 24, 2005

(65) Prior Publication Data

US 2006/0079928 A1 Apr. 13, 2006

Related U.S. Application Data

(63) Continuation-in-part of application No. 10/991,041, filed on Nov. 16, 2004.

(60) Provisional application No. 60/614,757, filed on Sep. 29, 2004.

(51) Int. Cl.
*A61M 29/00* (2006.01)

(52) U.S. Cl. .................................................... 606/200

(58) Field of Classification Search ................. 606/200
See application file for complete search history.

(56) References Cited

U.S. PATENT DOCUMENTS

| | | | | |
|---|---|---|---|---|
| 4,832,055 | A * | 5/1989 | Palestrant | 128/899 |
| 5,133,733 | A * | 7/1992 | Rasmussen et al. | 606/200 |
| 5,324,304 | A * | 6/1994 | Rasmussen | 606/200 |
| 5,836,968 | A * | 11/1998 | Simon et al. | 606/200 |
| 6,443,972 | B1 * | 9/2002 | Bosma et al. | 606/200 |
| 6,506,205 | B2 * | 1/2003 | Goldberg et al. | 606/200 |

* cited by examiner

*Primary Examiner*—Michael J. Hayes
*Assistant Examiner*—Christina Gettman

(57) ABSTRACT

A permanent blood clot filter which may be retrieved is provided. The blood clot filter includes a filter section and an alignment section. The filter section includes a filter hub and a set of filter legs whose downstream ends are connected to the filter hub. The filter legs extend axially and radially outwardly from the filter hub to form a conical configuration. The alignment section includes an alignment hub and a set of alignment ribs whose downstream ends are connected to the alignment hub and whose upstream ends are connected to the filter legs. The alignment ribs extend from the alignment hub radially outwardly and then further extend radially inwardly to provide centering of the filter.

34 Claims, 15 Drawing Sheets

PERMANENT BLOOD CLOT FILTER WITH CAPABILITY OF BEING RETRIEVED

CROSS REFERENCE TO RELATED APPLICATIONS

This application is a continuation-in-part of pending U.S. patent application Ser. No. 10/991,041, filed Nov. 16, 2004, which claims priority to U.S. Provisional Application No. 60/614,757, filed Sep. 29, 2004, all of which are incorporated herein by reference. This application also claims priority to pending U.S. patent application Ser. No. 10/991,013, filed Nov. 16, 2004, which claims priority to U.S. Provisional Application No. 60/583,274, filed Jun. 25, 2004, all of which are also incorporated herein by reference.

FIELD OF THE INVENTION

The present invention relates to a medical device apparatus and method for the capturing of thrombus. More particularly, the present invention relates to a permanent vena cava filter device with the capability of being retrieved and the methods of deployment and retrieval of the device.

BACKGROUND OF THE INVENTION

Vena cava filters are used to capture potentially fatal blood clots at an anatomical location where they may pose less risk of pulmonary emboli for the patient. Since the vast majority of pulmonary emboli originate from the lower body, filters are mainly placed in the inferior vena cava.

Vena cava filters have been in use since the 1960s in a variety of configurations. Early filters required open surgical placement (Mobin—Uddin Filter; Kimray—Greenfield filter). Since the late 1970s, improvements in delivery were made and numerous filters were developed for minimally invasive percutaneous placement. These filters included the Greenfield filter, the Gianturco Bird's Nest Filter, the Vena Tech LGM filter, the Simon Nitinol Filter and others. More recently, filters have been developed and marketed with the capability of retrieval after relatively long terms of implantation, which include the Bard Recovery Filter, the Cordis Optease Filter and the Cook Tulip Filter.

Although addressing some desirable characteristics of a filter, the majority of the IVC filters presently on the market do not satisfy other desirable characteristics of an optimal filter. The optimal device should capture blood clots while ensuring continued blood flow through the vessel. Blood flow disruption and turbulence often leads to thrombus formation and buildup at and around the filter. Studies have demonstrated that a conical filter configuration provides the optimal filtering efficiency. Filtering efficiency, for the purposes of this invention can be defined as the capability of the device to capture and retain clots of a pre-determined size, the ability to maintain blood flow through the filter in the presence of captured clots, and the capability of dissolving or lysing the clots caught in the filter. Conical designs force clots toward the center of the filter, allowing blood flow passage around the clot. Continued blood flow through the filter when a clot load is present ensures that captured clots are exposed to the lysing action of the blood flow.

Although conical filter configurations currently available on the market provide optimal filtering capabilities, these designs are prone to tilting and misalignment. When not in proper alignment, filtering ability is compromised. The central conical portion of the filter may tilt to the extent that it becomes embedded in the vessel wall. With retrieval designs, the retrieval hook is typically located at the central apex of the cone. If the tilting results in the retrieval hook coming in contact with the vessel wall, retrieval efforts become difficult or may even prevent removal. Laminar blood flow is disturbed, effective lysing of capture clots decreases, and thrombus build-up occurs.

To address the misalignment problem, filtering cones have been designed with alignment mechanisms to prevent tilting. For example, stent-like cage constructions have been designed to prevent the conical filter from becoming misaligned. The stent-like cage rests up against the vessel wall providing alignment to the filtering conical portion of the filter. This design, while optimizing centering of the filter, cannot be easily retrieved because of the difficulty in snaring and collapsing the cage. An example of this type of filter design is the Vena Tech LP filter which has a conical filtering segment adjoined to a zigzag stent base configuration for centering the cone within the vessel. Although this type of design combines the optimal filtering characteristics of a conical configuration with a non-tilting base, the device is not retrievable. The struts of the non-tilting base become incorporated into the vessel wall and cannot be easily disengaged and removed using standard snare removal techniques. The location of the stabilizing struts prevents the ability to withdraw the device into a sheath for removal.

It is possible to build a simple centering cage base/cone filter design that is retrievable by attaching the base to the filter segment in series. This design, while retrievable, is not practical due to the increased length of the device. The desired length of a typical IVC filter is between 4 and 6 centimeters. Longer lengths are undesirable because of the limited implantation space of the vena cava. For example, in some cases it is necessary to deploy a second filter due to malfunction of the initially placed filter. Shortening the filter segment may make the overall device length acceptable, but may result in sub-optimal filter strut angles. Alternatively, shortening the centering cage segment may compromise the alignment function of the device.

IVC filters should be capable of remaining in the vessel for long periods of time, and in some cases, indefinitely. The filter should be designed as a permanent filter so as not to migrate from its originally deployed position while still allowing for optional retrieval of the filter. Thus the vessel wall engagement mechanism should be designed so as to maintain position even under a heavy clot load and yet allow easy and atraumatic disengagement from the vessel during retrieval. Longitudinal movement of the filter has traditionally been prevented by configuring filter ends with hooks that embed in the vessel wall.

Because of concerns with permanent implantation of filters, including possible migration and structural integrity over long time periods, there is an emerging trend for filters that can optionally be retrieved after a specified period of time. The optimal filter should be designed as a permanent filter that may be optionally retrieved. Specifically, the design should have fixation characteristics that ensure the device will not migrate while allowing retrieval if desired. Thus, the wall-engaging mechanism should also be designed to allow percutaneous removal of the device without significant trauma or damage to the vena cava wall even after neointima overgrowth has occurred. These two disparate clinical requirements, long-term fixation and atraumatic removal, are difficult to achieve in a single filter design.

Some prior art filter designs have utilized aggressive anchoring mechanisms to ensure fixation, but these designs are difficult to remove. Conversely, designs that limit wall contact are easier and less traumatic to disengage from the vessel, but may be more prone to migration. In addition, the optimal filter will be designed to automatically compensate for changes in the diameter of the vena cava which occur as part of the normal respiration process. Prior art filters with less aggressive fixation may be vulnerable to detachment from the vessel wall as the vena cava diameter changes.

As with all long-term or permanent implant devices, the optimal device design will maintain structural integrity of the device for the duration of implantation. Although rare, filter fractures have potentially fatal complications including filter migration into the right atrium and pulmonary embolism caused by compromised filtering efficiency. The optimal filter device should have minimal weld or other attachment points which are more susceptible to fatigue over extended periods of time. In addition to long term performance characteristics, it is desirable to provide an IVC filter that is simple and inexpensive to manufacture without requiring complicated assembly processes that might compromise the long-term integrity of the device or increase the overall cost of the device.

Another desirable characteristic of the optimal filter is a small deployment and retrieval system. A design that minimizes the delivery device diameter will result in a smaller insertion site and reduced risks of bleeding, site thrombus and other complications of percutaneous punctures. The optimal vena cava filter should not only be easy to deploy using minimally invasive percutaneous techniques, but also be repositionable during initial deployment. Many filters are designed for ease of deployment but do not allow for repositioning during delivery. Finally, the optimal filter will be easily retrieved using a simple retrieval system.

Therefore, it is desirable to provide a permanent vena cava filter with the capability of being retrieved at any time after implantation. It is also desirable for the filter to have superior structural integrity that prevents fracture or other structural fatigue to the device over indefinite implantation times, but should also be sufficiently small to allow for easy retrieval using a small, simple retrieval system. It is also desirable to provide a filter that provides secure and stable fixation against the vessel wall for extended periods of time while also allowing for non-traumatic removal when desired. It is also desirable to provide a permanent filter that does not easily tilt or otherwise become misaligned.

SUMMARY OF THE DISCLOSURE

A blood clot filter comprising a filter section and an alignment section is provided. The filter section includes a filter hub and a set of first filter legs having downstream ends connected to the filter hub. The first filter legs extend axially and radially outwardly from the filter hub. The alignment section includes an alignment hub and a set of alignment ribs having downstream ends connected to the alignment hub and upstream ends connected to the first filter legs. The alignment ribs extend from the alignment hub radially outwardly and then further extend radially inwardly.

In another aspect of the invention, each alignment rib includes two branches each having a downstream end and an upstream end. The downstream ends of the two branches are connected to each other. The upstream end of one branch is connected to one of the first filter legs and the upstream end of the other branch is connected to an adjacent one of the first filter legs.

In another aspect of the invention, the filter includes a set of second filter legs having downstream ends connected to the filter hub and being spaced from the first filter legs. The second filter legs are positioned under the alignment ribs such that the alignment ribs limit radially outward movement of the second filter legs.

In another aspect of the invention, a method of retrieving the filter is provided. While the filter is deployed in a vessel, the alignment hub is captured. This can be done using a snare, for example. Then, a sheath is moved over the alignment ribs so as to cause the second filter legs to be pushed radially inwardly by the alignment ribs. The sheath is further moved over the first filter legs to cause them to be pushed inwardly.

BRIEF DESCRIPTION OF THE DRAWINGS

FIG. 5A is a plan view of the outer tubular body of the vena cava filter device of the present invention in a non-expanded state.

FIG. 5B is an enlarged plan view of the inner tubular body of the vena cava filter device of the present invention in a non-expanded state.

FIG. 5C is an enlarged sectional view of the retrieval hook subassembly of the vena cava filter device.

FIG. 7A is a sectional view of the non-expanded filter within the deployment system prior to deployment in the vein.

FIG. 7B is a plan view of the filter and deployment system with the filter legs partially deployed.

FIG. 7C is a plan view of the filter and deployment system after full deployment in the vein prior to detachment from the deployment system.

FIG. 7D is a plan view of the filter and deployment system after the filter has been detached from the deployment system.

FIG. 8A is a plan view of the method of retrieval of the vena cava filter device depicting capture of the device by a snare sheath.

FIG. 8B is a plan view of the method of retrieval of the vena cava filter device depicting retraction of the alignment structure into the sheath.

FIG. 8C is a plan view of the method of retraction of the filter legs into the sheath.

FIG. 8D is a plan view of the method of retrieval depicting the completely collapsed filter within the retrieval sheath.

DETAILED DESCRIPTION OF THE INVENTION

Figure 1:
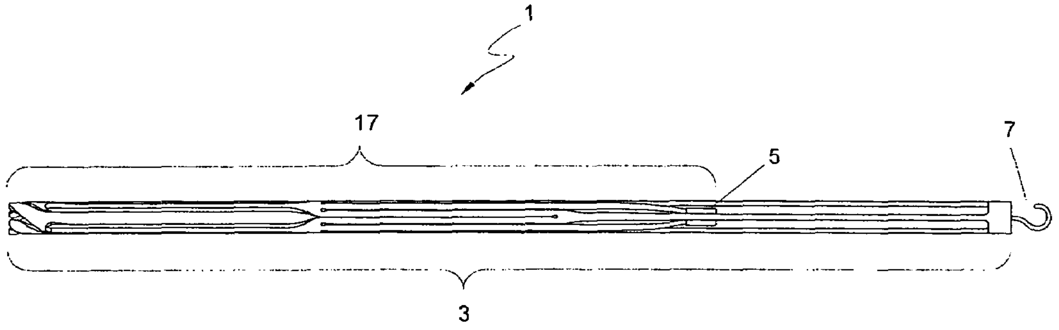
FIG. 1 is a plan view of one exemplary embodiment of a vena cava filter device in a collapsed, non-expanded state according to the present invention.
Figure 2:
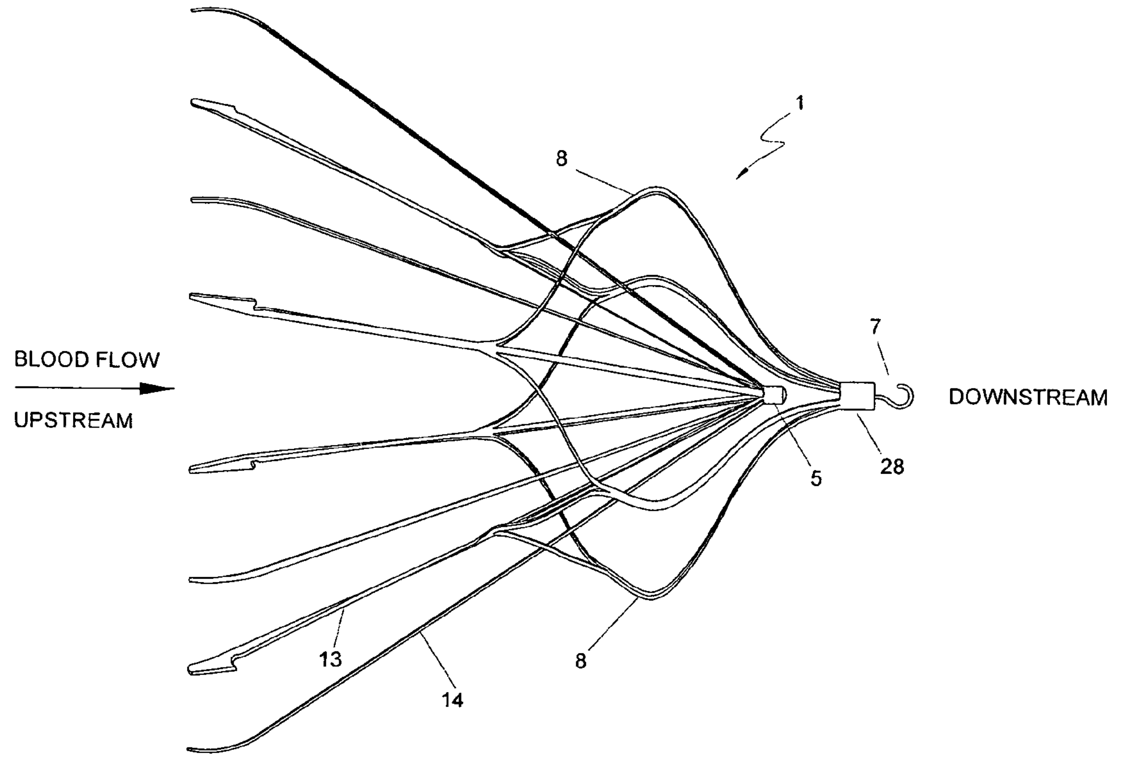
FIG. 2 is a plan view of the vena cava filter device of FIG. 1 in a deployed, expanded state.

For the purposes of the present application, the terms upstream and downstream refer to the direction of blood flow. Accordingly, blood flows from an upstream direction towards a downstream direction. Referring to FIG. 1, there is shown an embodiment of the present invention in a plan view of a non-expanded vena cava filter device 1. Although not shown in FIG. 1, the filter is held in a collapsed, non-expanded state by a sheath, catheter or other tubular construct. When deployed in the path of the blood stream, typically in the vena cava vein, the filter 1 expands outwardly as shown in FIG. 2 to capture blood clots of a predetermined size and prevent them from traveling further upstream.

The filter 1 is formed from laser-cut cannulas or tubes. The tubes are preferably of a material with shape-memory characteristics such as nitinol to allow expansion from constrained state shown in FIG. 1 to a deployed configuration at body temperature as shown in FIG. 2. Nitinol is an alloy well-suited for vena cava filters because of its shape-memory characteristics, which enables it to return to a pre-determined expanded shape upon release from a constrained position. Other shape memory metals such as stainless steel may be used to form the filter 1.

Referring to FIG. 1, the filter 1 is comprised of a outer tubular body 3, a inner tubular body 17 and a retrieval hook subassembly 7. The outer tubular body 3 is configured to provide the primary anchoring, filtering and centering functions of the filter 1 when expanded. Outer tubular body 3 is preferably dimensioned with an outer diameter of 0.072 inches and an inner diameter of 0.052 inches, although other configurations are possible. In the unexpanded configuration, the length of outer tubular body 3 is approximately 6 centimeters in length. When expanded, this length is reduced by approximately 1 centimeters to 5 centimeters, depending on the diameter of the inner vena cava wall. The outer tubular body 3 is laser cut to a pattern that forms the primary filtering legs and alignment ribs, as will be described in more detail below.

Assembled coaxially within the lumen of outer tubular body 3 is an inner tubular body 17, with an outer dimension in the range of 0.048 to 0.050 inches to allow for sufficient annular space between the two tubular bodies during assembly, deployment and retrieval. Inner tubular body 17 is also laser-cut to a pattern that forms the secondary legs structure which function to increase thrombus-capturing efficiency of the filter. Tube 17 is approximately 4.4 centimeters long in the unexpanded configuration terminating at the downstream end with conical filtering hub 5 and at the upstream end with free leg ends. As shown in FIG. 1, the inner tubular body 17 is positioned within outer tubular body 3 along the longitudinal axis such that the upstream ends of each tube 3 and 17 are flush with each other. Because the length of outer tubular body 3 is at least one centimeter longer than the inner tube 17, when assembled, inner tubular body 17 is positioned completely within the lumen of outer tubular body 3, terminating at conical filtering hub 5.

The final assembly component of the vena cava filter 1 of the current invention is retrieval hook subassembly 7 located at the downstream end of the filter. The hook functions to allow retrieval of the vena cava filter 1 by use of a snare or other retrieval device. It is welded or otherwise connected to the downstream end of the outer tubular body 3.

FIG. 2 depicts the vena cava filter 1 in an expanded, deployed position. Outer tubular body 3 is comprised of the outer tubular body hub 28, alignment ribs 8 and primary filtering legs 13. The retrieval hook subassembly 7 is connected to outer tubular body 3 and extends downstream from outer tubular body hub 28. The inner tubular body 17 is within the expanded outer tubular body 3 and is comprised of an conical filtering hub 5 and secondary filtering legs 14.

Figure 3A:
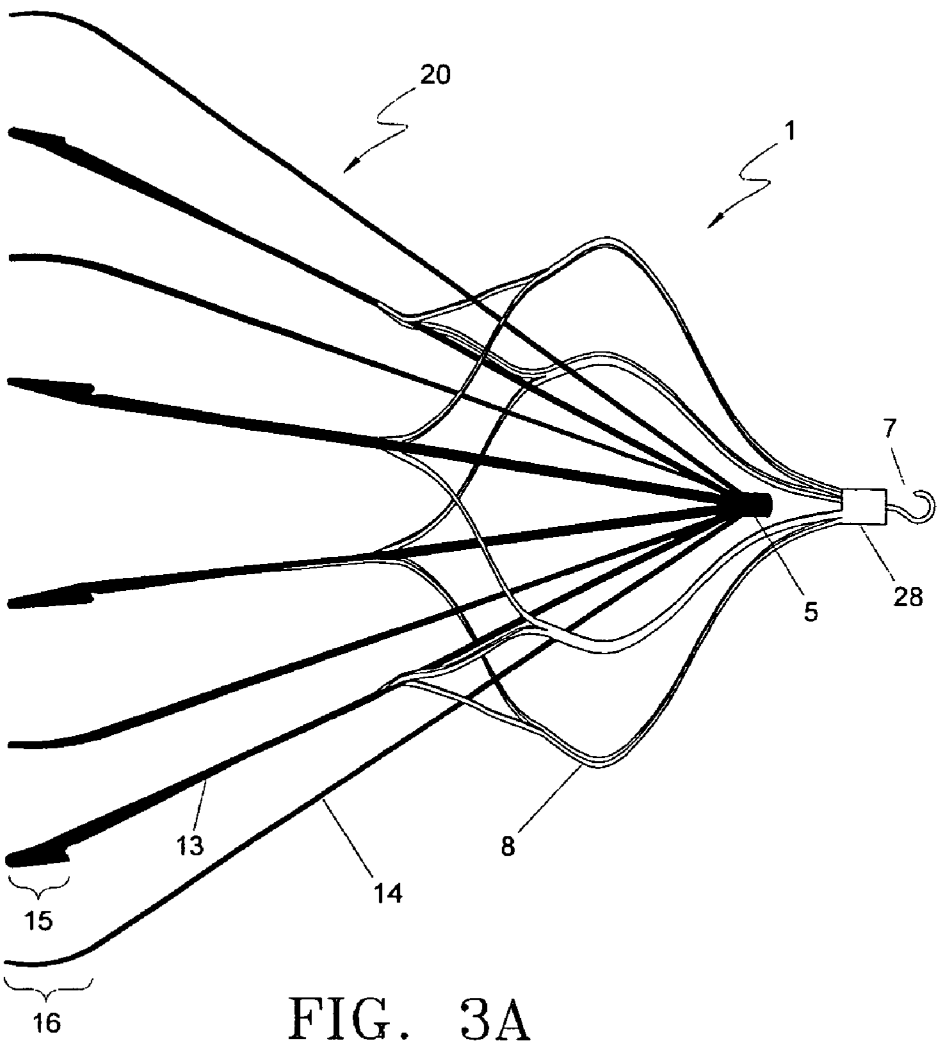
FIG. 3A is a plan view of the vena cava filter device of FIG. 2 highlighting the conical filtering structure 20.
Figure 3B:
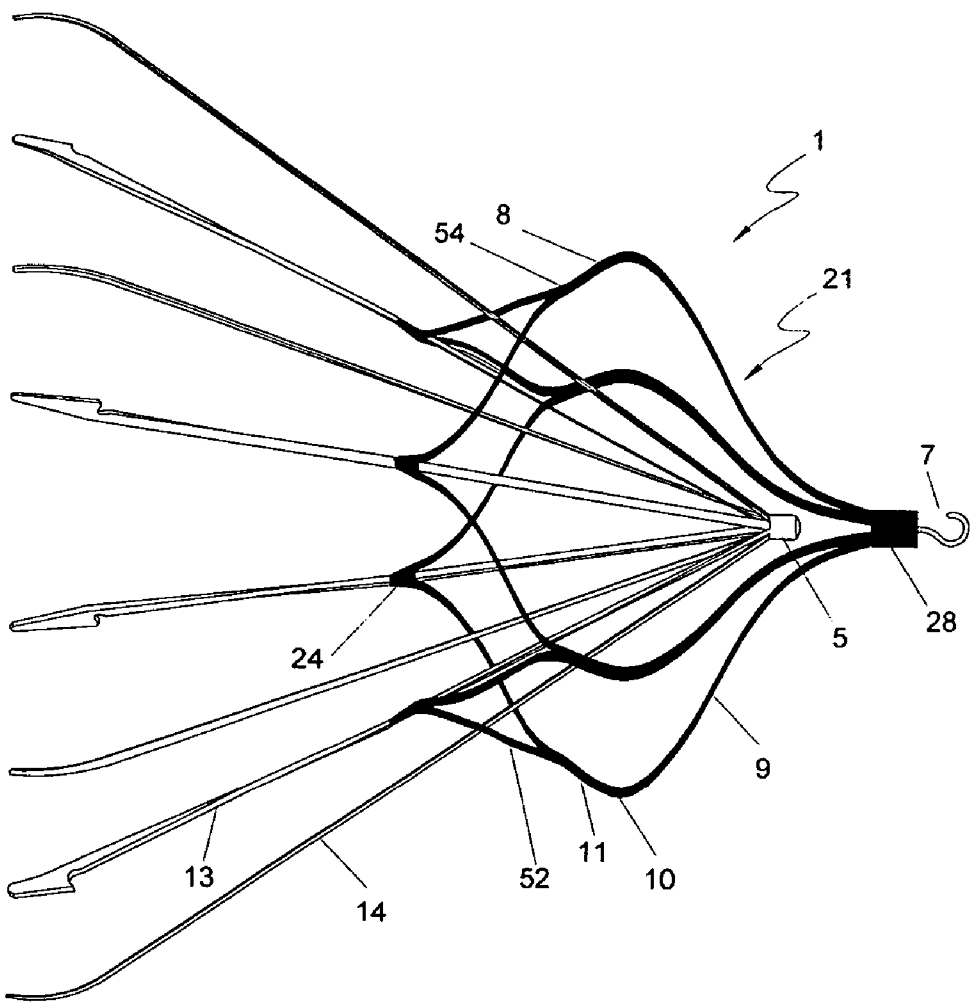
FIG. 3B is a plan view of the vena cava filter device of FIG. 2 highlighting the alignment structure 21.

Referring now to FIGS. 3A and 3B, an expanded filter 1 is shown in a plan view highlighting the two main structural elements of the filter. FIG. 3A highlights the conical filtering structure (filter section) 20 and FIG. 3B highlights the alignment structure (alignment section) 21 of the vena cava filter 1. The conical filtering structure 20 performs the primary clot capturing and lysing function of the device as well as primary anchoring function to prevent migration of the filter in a downstream direction. The alignment structure 21 provides central alignment of the conical filtering structure 20 within the vessel lumen and ensures symmetrical deployment and retrieval of the primary filtering legs 13 and secondary filter legs 14.

The conical filtering structure 20 highlighted in FIG. 3A is comprised of primary filtering legs 13 and secondary filter legs 14. Each primary filtering leg 13 and secondary filter leg 14 extends radially and outwardly in an upstream direction from the conical filtering hub 5. In the preferred embodiment, the axial diameter of the expanded filter at the upstream leg ends is typically 40 millimeters to accommodate larger cava diameters. This diameter will vary depending on the diameter of the patient's vena cava.

The filtering legs are eight in number, with four being primary filtering legs 13 with upstream wall-engaging portion 15 and four being secondary filtering legs 14 that contact the vessel wall but do not have wall-penetrating portions. Primary filtering leg 13 terminates at the upstream end in a wall-engaging portion 15. Each leg 13 is approximately 0.020 to 0.030 inches wide with a preferred thickness of 0.010 inches corresponding to the wall of outer tubular body 3. In one embodiment, the upstream end portion of primary filtering leg 13 may be of a reduced width to facilitate formation of the wall-engaging portion 15.

Figure 6A:
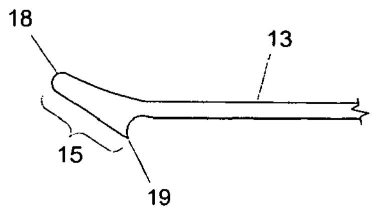
FIG. 6A is an enlarged plan view of the wall-engaging portion of the primary filtering legs.

In the embodiment shown, the device 1 contacts the vessel wall on an upstream plane at wall-engaging portion 15 of the primary filter legs 13. The wall-engaging element 15 functions to positively anchor the legs 13 in the vena cava wall to prevent downstream migration of the device. FIG. 6A depicts an enlarged view of the wall-engaging portion 15, which is comprised of a foot 18 having a barb 19. The overall length of wall-engaging portion 15 is typically 3 millimeters, extending from the tip of the foot 18 to the tip of the barb 19, but may range from 1.5 to 5 millimeters. The length of the barb 19 from the tip to the central aspect of the filtering leg 13 may be dimensioned at about 0.5 to 1.5 millimeters in length, preferably 0.5 millimeters to ensure stable securement in the vessel wall without penetrating through the vena cava into the surrounding tissue. The foot 18 rests parallel to and on the surface of the vessel wall, providing a platform that limits the depth of penetration of the barb 19 during normal diameter changes in the vena cava.

Figure 6B:
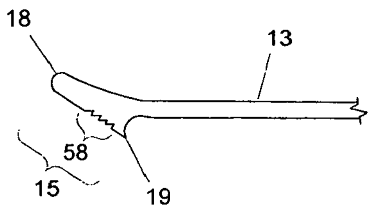
FIG. 6B is an alterative embodiment of the wall-engaging portion of the primary filtering legs shown in an enlarged plan view.

An alternative embodiment of the wall-engaging portion 15 of primary filter leg 13 is illustrated in FIG. 6B. The wall-engaging element 15 includes barb 19 which engages the vessel wall to stabilize the device and specifically to prevent antegrade migration within the vena cava. In the FIG. 6B embodiment, the foot 18 includes a series of small, sharpened projections or barbs 58 located on the barb side of the foot 18. These projections are angled in an opposite direction from the barb 19 tip and are approximately 0.2 millimeters in height. In other words, the series of smaller barbs 58 generally point in the upstream direction. These projections function to prevent upstream migration of the device when blood is flowing in a retrograde direction.

Figure 5A:
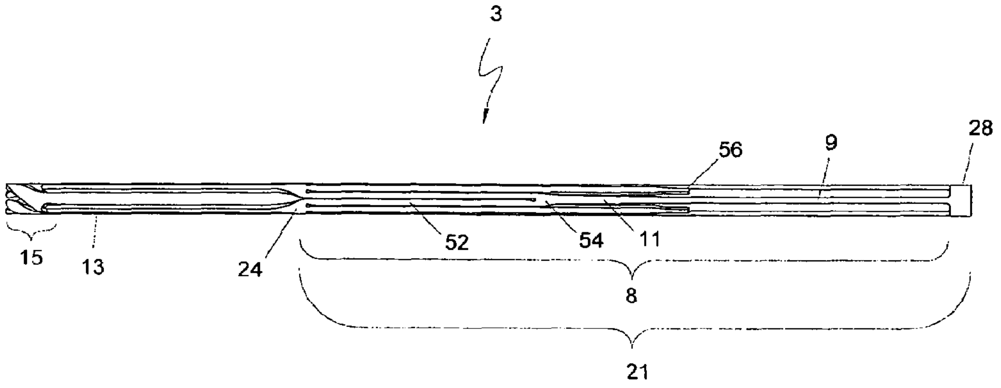
FIG. 5A-5C depict the three assembly components of the vena cava filter device.
Figure 5B:
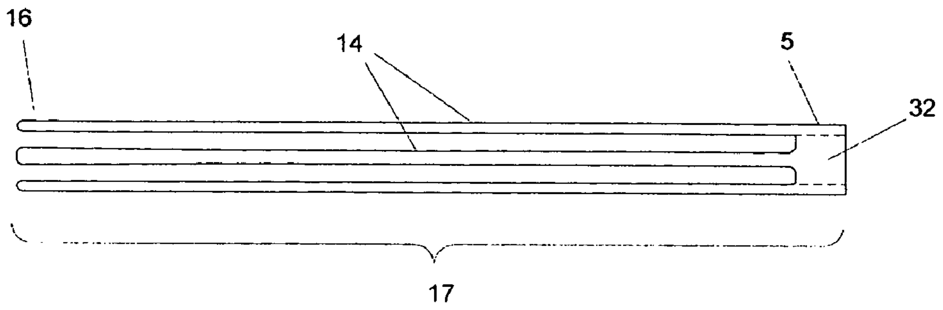

Referring once again to FIG. 3A, the secondary filtering legs 14 are formed from an inner tubular body 17, which is depicted in detail in FIG. 5B. The inner tubular body 17 is preferably laser-cut in a pattern to form secondary filtering legs 14 approximately 0.020 to 0.030 inches wide. The thickness of the legs 14 is 0.010 inches corresponding to the wall of inner tubular body 17. In the preferred embodiment, the secondary filtering legs 14 extend radially outward from the longitudinal axis of the filter terminating in a curved end 16 which contacts and rests against the vessel wall but does not penetrate it. These secondary filtering legs 14 provide enhanced filtering capabilities in addition to providing a secondary non-penetrating filter anchoring function. The curved end 16 of each secondary filtering leg 14 is approximately 1 cm long with a radius of 16 millimeters and as such is contoured to ensure non-penetrating wall contact and easy, non-traumatic disengagement during retrieval. The curve allows the secondary filtering leg 14 free end to smoothly disengage and slide out away from the vessel wall when the device is being retrieved.

Thus conical filtering structure 20, with both primary and secondary filtering legs, performs the clot capturing function of the filter by capturing the clots within the filter legs and forcing the clots toward the conical filtering structure hub 5 which is located at the center of the vessel. Clots are captured and funneled into the conical apex where they are optimally exposed to the lysing action of the blood flow. The conical filtering structure also performs the primary and secondary vessel anchoring functions by means of the wall-engaging portion 15 of the primary filtering leg 13 and the non-penetrating curved end 16 of the secondary filtering legs 14.

The alignment structure 21 is highlighted in FIG. 3B. The alignment structure 21 provides central alignment of the conical filtering structure 20 within the vessel and ensures symmetrical deployment and retrieval of primary filtering legs 13 and secondary filter legs 14. The alignment structure 21 is formed of individual alignment ribs 8, which together form a series of enclosed loops. An enclosed loop configuration is advantageous over prior art filters with centering structures comprised of individual legs with free ends. Alignment structures with individual legs have been known to become entangled or otherwise misaligned and fractured during deployment and retrieval. The enclosed loop design of the current invention has no free ends and thus is not prone to misalignment or entanglement with other interventional devices. Because the structure is fabricated by a laser cutting process with no welded joints, the design also provides enhanced structural integrity and strength over free-ended leg configurations.

In the preferred embodiment, the alignment ribs 8 are four in number, although the number of ribs 8 is dependent on the number of primary filtering legs 13, with one rib for each leg. Each alignment rib 8 is approximately 0.014 inches wide with a thickness of 0.010 inches corresponding to the wall of outer tubular body 3.

In its expanded state, the maximum diameter of the alignment structure 21 is typically 22 millimeters, although other dimensions are possible. Accordingly, some or all of the alignment ribs 8 will rest against the inner wall of the vessel if the vessel is 22 millimeters or less. For vena cava vessels larger than 22 millimeters, the alignment ribs 8 will only contact the vessel wall if the filter 1 begins to tilt away from the center of the lumen. When alignment ribs 8 contact the vessel wall, further tilting and misalignment are prevented. Thus alignment of the filtering structure 20 within the vessel is achieved by alignment ribs 8 contacting the vessel wall, whether that contact is continual (as is the case for smaller diameter vessels) or occurs only when and if the filter 1 begins to tilt (as is the case for larger diameter vessels). The alignment structure also eliminates the problem with some prior art filters becoming tilted to the extent that the retrieval hook element 7 embeds into the vessel wall.

Each alignment rib 8 is comprised of an undivided alignment rib downstream portion 9, a vessel wall contact portion 10, an undivided upstream portion 11 and alignment rib extension (branch) portions 52. The alignment rib downstream portion 9 extends radially outward from the outer tubular body hub 28 to the rib wall contract portion 10. Alignment rib contact portion 10 preferably has a gradually curved contour to provide a retaining pressure when against the vessel wall that is dispersed over a larger surface area than point contact designs. The rounded contour of alignment rib contact portion 10 also provides secondary filter anchoring without the risk of puncturing or otherwise damaging the vessel wall at the contact location. In addition, the curved profile of the alignment rib 8 provides flexible wall contact area that accommodates changes in the diameter of the vena cava without piercing or otherwise damaging the vessel wall.

Optionally, the central-facing aspect (inner surface) of alignment rib contact portion 10 may be sharpened or may have a longitudinal pointed edge to facilitate removal. If filter 1 is deployed in a smaller size vena cava, the alignment rib contact portion 10 may remain in contact against the vessel wall for the duration of implant. In this situation, the endothelial lining of the inner vessel wall may grow over and incorporate rib alignment contact portion 10 within the vessel wall. Central-facing aspect of rib contact portion 10, if sharpened, will cut through the endothelial overgrowth during device withdrawal so as to minimize vessel wall damage and trauma.

The alignment rib upstream portion 11 extends from the contact portion 10 inwardly toward the vessel center. Upstream portion 11 splits into two alignment rib extensions (branches) 52 at alignment rib branch point or junction point 54. The two alignment branches 52 of alignment rib 8 extend radially inward and terminate at connecting point 24 on an adjacent primary filtering leg 13. The series of alignment extensions 52 form a zigzag pattern that provides a stabilizing platform for the primary filter legs 13 and that ensures the conical filter section is maintained in the central alignment with the vessel throughout the implantation period. The zigzag pattern also functions to provide alignment of the secondary filtering legs 14. Each secondary filtering leg 14 extends radially outward between two alignment branches 52 of an alignment rib. The positioning of the secondary filtering leg 14 between two alignment branches limits movement to the space between two adjacent alignment branches 52.

The positioning of the secondary filtering leg 14 within the alignment branches 52 also prevents the legs from prolapsing in a downstream direction when the filter is under a heavy clot burden. Specifically, the legs are restrained within the two alignment branches 52 at junction point 54 and are thus prevented from further downstream movement and the junction point 54 limits the radially outward movement. Because of this design, the secondary filtering legs 14 do not require fixation barbs on the leg ends to stay in correct alignment against the vessel wall. As such, the secondary filtering legs may optionally be configured to be of a reduced width relative to the primary filtering legs 13 without compromising the overall structural integrity of the device. As an example, the width of the individual secondary filtering may be as small as 0.010 inches and still impart the necessary strength, filtering and positioning characteristic required while implanted within the body. This design also allows the secondary filtering legs 14 to be thinner, lighter and more flexible than the primary legs.

This novel alignment design thus overcomes prior art problems with cone tilting and the resulting complications of blood flow turbulence, compromised lysing capability and thrombus buildup. In one novel aspect of the invention, centering of primary filtering legs 13 and secondary filtering legs 14 within in the vessel is achieved with the alignment structure 21 which substantially overlaps the conical filtering structure 20 and thus does not significantly extend the overall length of the filter device 1. The interconnecting arrangement of the alignment ribs 8 to each other ensures that all primary filtering legs 13 and secondary filtering legs 14 are symmetrically deployed around the inner vessel wall. Leg crossing or entanglement during or after deployment is avoided by the interconnecting design of the alignment ribs 8, which ensure equal spacing is maintained between each apex at both the upstream and downstream ends of the filter. The symmetrical deployment, anchoring and alignment features of this design allow the filter to be consistently placed in vena cavas of varying dimensions and shapes.

Figure 4:
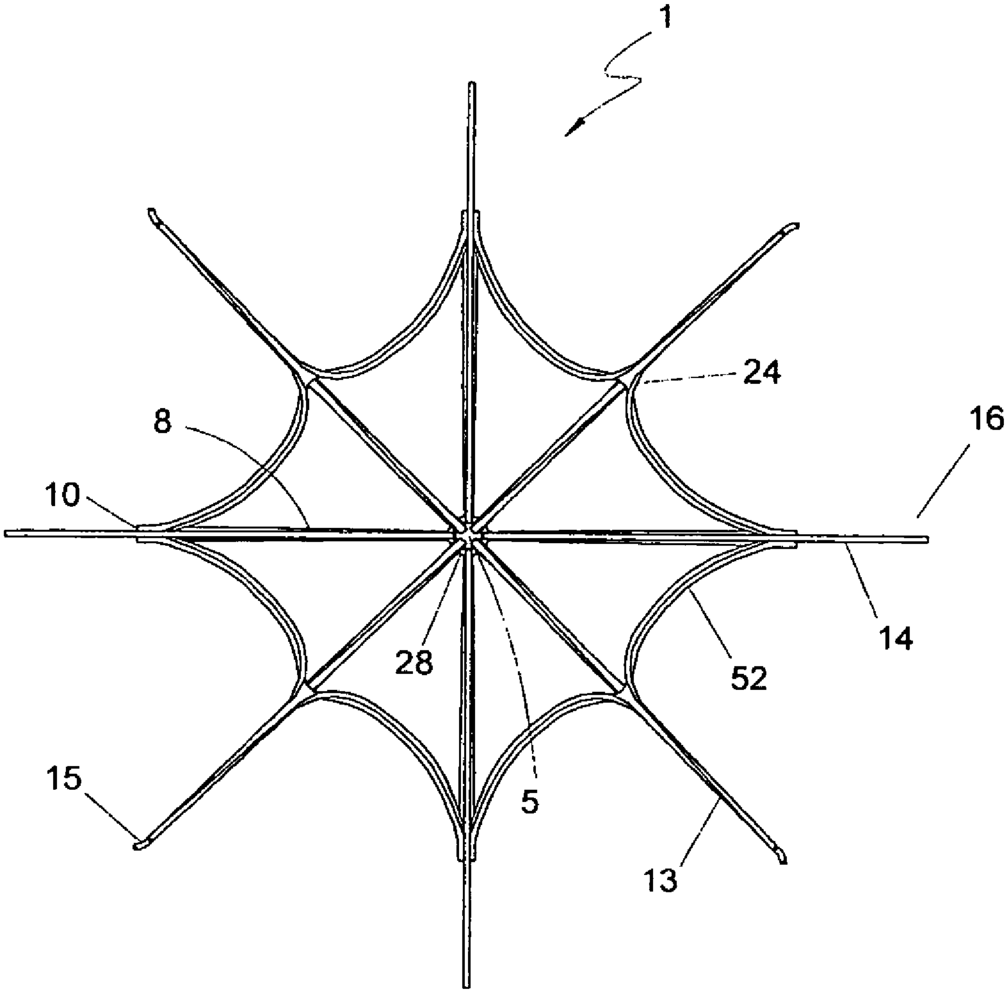
FIG. 4 is an upstream end view of the expanded vena cava filter as depicted in FIG. 2.

Referring now to FIG. 4, an enlarged end view of the filter device 1 in an assembled and expanded state is shown from an upstream end view. The alignment ribs 8 self-center the device 1 through alignment rib wall contact portion 10. Primary filtering legs 13 extend radially outward from the conical filtering hub 5 to contact the vessel at a second upstream plane. The alignment ribs 8 intersect primary filtering legs 13 at connecting point 24 and act to prevent the legs from crossing each other during deployment and implantation. The secondary filtering legs 14 are aligned with the junction point 54 in a radial direction and are allowed to move within the space between two alignment rib extension portions 52, but are restricted from further movement. As shown in FIG. 4, these legs provide an additional level of cava filtration.

The alignment ribs 8 extend radially outward from the outer tubular body hub 28 to bisect the cross-sectional area between two adjacent primary filtering legs 13 providing a further level of downstream cava filtration. Thus, alignment ribs 8 provide a supplemental filtering mechanism by capturing thrombus that might otherwise pass through the area between two adjacent filtering legs 13 and cause a life-threatening pulmonary embolus. Wall-engaging portion 15 of the filter legs provides the primary fixation against downstream migration of the device 1. Alignment rib contact portion 10 and secondary leg ends 16 provide non-penetrating secondary anchoring fixation.

Figure 5C:
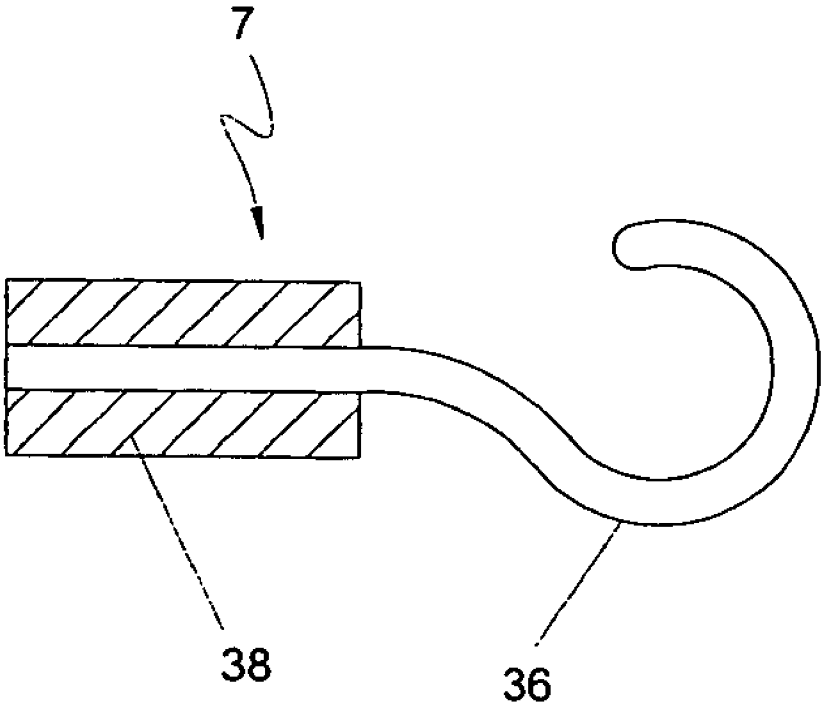

Turning now to a detailed description of subassembly components of the device, FIG. 5A-5C respectively depict the outer tubular body 3, the inner tubular body 17 and the retrieval hook subassembly 7 in a pre-assembly state. FIG. 5A is a plan view of the outer tubular body shown in a non-expanded state after laser cutting. FIG. 5A illustrates the preferred pattern to which the tube is laser-cut to form the alignment structure 21 and the primary filtering legs 13.

During manufacture of the device 1, outer tubular body 3 is first cut into the desired configuration using laser-machining techniques commonly known in the art. Other cutting techniques such as photo or acid etching may be used to form the desired cut patterns for the outer tubular body 3. Prior to final manufacturing assembly, the outer tubular body 3 is approximately 6 centimeters in length. The outer diameter of the tube is preferably 0.072 inches to accommodate insertion of the device through a 6F sheath. With an inner diameter of preferably 0.051 inches, the outer tubular body 3 has a wall thickness of approximately 0.010 inches. Material is cut away from the tube 3 in a pre-determined pattern to form the alignment structure 21 and primary filtering legs 13 without requiring any weld joints or other mechanical connection points.

Primary filtering legs 13 extend from the wall-engaging portion 15 to the downstream filter leg ends 56, which are free, unconnected ends in the unassembled state. As will be explained in more detail below, the filter leg ends 56 may be of a reduced diameter to facilitate insertion into conical filtering hub 5 of the inner tubular body 17. The main portion of primary filtering leg 13 is typically 0.020 inches wide tapering down to approximately 0.010 inches wide at the leg end 56. The reduced width portion of leg end 56 is approximately 0.28 inches in length.

The alignment structure 21 is comprised of outer tubular body hub 28 and alignment ribs 8. Prior to the shape-forming process which will be described in more detail below, the alignment structure is substantially straight and un-curved. Alignment rib 8 extends from the uncut outer tubular body hub 28 to connecting point 24 on the primary filter leg 13 and includes the alignment rib downstream portion 9, the alignment rib upstream portion 11, the alignment rib branch point 54 and the alignment rib extensions 52.

Referring now to FIG. 5B, the inner tubular body 17 is depicted after the laser-cutting process and prior to the shape-forming step. Shown in a plan view, the inner tubular body is typically 4.4 centimeters in length with an outer diameter of 0.048 inches allowing it to be freely assembled within the lumen of the outer tubular body 3, which has an inner diameter of approximately 0.051 inches. The laser-cutting pattern forms the secondary filtering legs 14 and optionally the radius on the leg ends 16, which are un-curved prior to the annealing process. The conical filtering hub 5 represents the uncut portion of the tube and is approximately 0.060 inches in length. Each secondary filtering leg 14 is approximately 0.020 inches in width with a depth of approximately 0.010 inches corresponding to the wall of the inner tubular body 17.

The conical filtering hub 5 functions as a hub holding the downstream filter leg ends 56 of the outer tubular body 3 together to create the conical apex of the conical filtering structure 20. Inner tubular body 17 is preferably of a same material as the outer tubular body 3 for ease of assembly. During assembly, the downstream filter leg ends 56 (see FIG. 5A) are inserted into the lumen 32 of conical filtering hub 5 and spot-welded or otherwise permanently bonded together to form the conical apex. Leg ends 56 may be of a reduced width relative to the remainder of primary filtering leg 13 to facilitate insertion within lumen 32. The reduced taper also ensures that the welding process involves a lesser amount of leg material, so as to avoid a material buildup at the hub area.

FIG. 5C depicts an enlarged section view of the retrieval hook subassembly 7. The retrieval hook subassembly 7 is the mechanism by which the device 1 is captured and drawn into the retrieval system as will be described in greater detail below. Retrieval hook subassembly 7 is comprised of an engaging element such as a retrieval hook 36 and hook bushing 38 which are welded or otherwise permanently bonded together. Bushing 38 is received within the lumen of outer tubular body 3 at hub 28 so as not to increase the overall outer profile of device 1. Specifically, the outer diameter of the bushing 38 of the retrieval hook 7 will not exceed 0.052 inches, which is the inner diameter of the outer tubular body 3. In addition, the arc diameter of the retrieval hook 36 is designed to be equal to or less than the outer tubular body 3 outer diameter. The bushing 38 and retrieval hook 36 may be spot welded together or other bonding techniques may be used to attach the two components. The completed retrieval hook subassembly 7 is then inserted into the lumen of hub 28 of the outer tubular body 3 and welded or otherwise connected.

To manufacture the device, the outer tubular body 3 and inner tubular body 17 are first cut into the desired configuration using laser-machining techniques commonly known in the art. Other cutting techniques such as photo or acid etching may be used to form the desired cut patterns for both the inner and outer tubular bodies. Material is cut away from the tubes in a pre-determined pattern to form the desired configurations. The outer tubular body 3 and inner tubular body 17 are then annealed or heat-treated to form the expanded deployment shape of FIG. 2. As part of the shape-forming process, the upstream of the filter legs 13 are twisted or rotated approximately 90 degrees. This twisting step ensures that when deployed the barbs 19 are presented radially outward relative to the downstream portion on the primary filtering leg 13 to actively engage the vessel wall.

To assemble the filter, the conical filtering hub 5, shown in detail in FIG. 5B, is positioned over the downstream end of the free primary filtering legs 13, drawing them together to form a conical configuration. Hub 5 is welded, press-fit or otherwise bonded to the downstream ends of primary filtering legs 13. The retrieval hook subassembly 7 is also welded or otherwise bonded to the upstream end of the outer tubular body 3 using techniques commonly known in prior art. The assembled filter may be electropolished or otherwise processed to ensure a smooth surface finish. The filter 1 is then constrained within a sheath or catheter to the non-expanded profile as shown in FIG. 1. Thus, the method of manufacturing the filter of the current invention is a simple process utilizing a highly-reliable laser-cutting process that requires only minimal welds or other connection points and is easy and cost-effective to assemble.

Figure 7A:
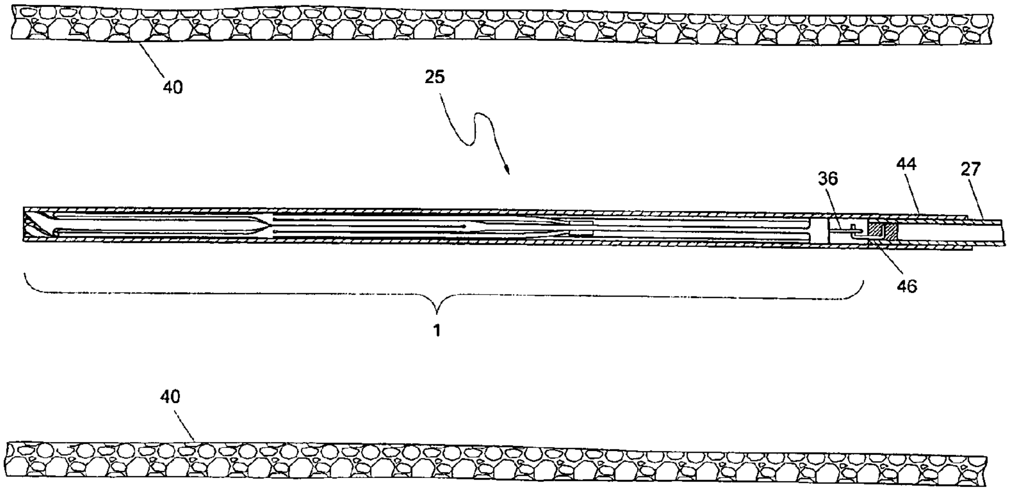
FIGS. 7A through 7D illustrate a method of deploying the vena cava filter within the vessel.

The method of filter deployment will now be described with reference to FIG. 7A-7D. To place the filter percutaneously, a deployment device 25 containing the filter 1 in a collapsed state is introduced through a standard introducer sheath (not shown) through the jugular vein into the vena cava wall 40. FIG. 7A depicts the filter 1 collapsed within the deployment device 25 prior to deployment in the vessel. The deployment device 25 is preferably a two-component coaxial tube system comprising an inner deployment member 27 and outer deployment member 44. The outer deployment member 44 coaxially surrounds the inner deployment member 27. Outer deployment member 44 provides an outer housing to retain the filter 1 in a constrained/collapsed position prior to deployment and also functions to deploy the filter 1 when the outer deployment member 44 is retracted.

The distal end of the inner deployment member 27 is releaseably connected to the retrieval hook 36 by the inner deployment tube connector element 46. Inner deployment tube connector element 46 may be configured as a hook mechanism as shown in FIG. 5C or other releasable connection means commonly used in the art. The tubular construction of the filter 1 minimizes the deployment device 25 diameter. In the preferred embodiment, the deployment device 25 will fit within a 6 French delivery system, providing a small insertion site and less trauma to the patient.

Once correct positioning within the vena cava has been confirmed, the filter 1 is controllably deployed in the vessel. In one embodiment, the filter 1 is deployed through a series of two steps. In this staged deployment, the filter legs and the alignment ribs 8 are unsheathed, exposing the entire filter 1. After the filter is fully expanded and engaging the vessel wall 40 on two planes, a second step separates the deployment device 25 from the filter 1. The two steps are sequentially performed in a smooth motion.

Figure 7B:
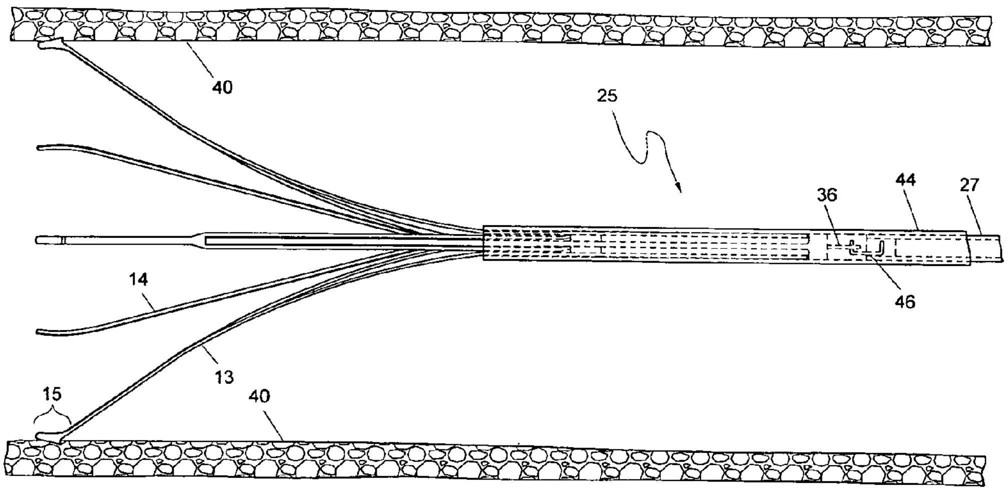
Figure 7C:
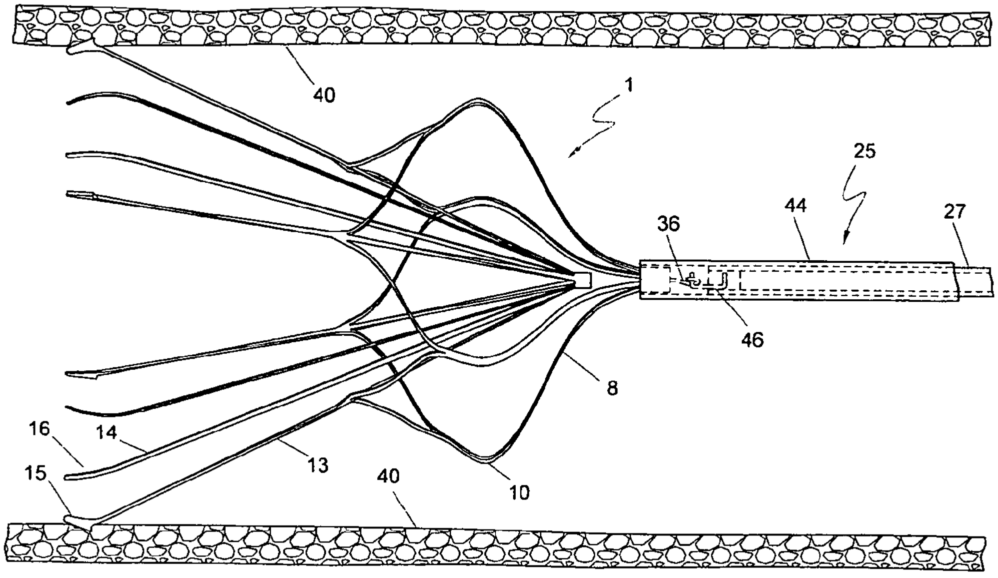

FIGS. 7B and 7C illustrate the first deployment step in which the filter 1 is exposed after retraction of the outer deployment member 44. As shown in FIG. 7B, the outer deployment member 44 is retracted while maintaining the position of the inner deployment member 27. As the outer tube 44 is retracted, the upstream section of the filter 1 is uncovered and expands to its pre-formed shape, causing the primary filter legs 13 to engage the vena cava wall 40. Specifically, wall-engaging portion 15 of the primary filtering legs 13 will contact and advance into the vena cava wall 40. The secondary filter legs 14 also contact and rest against the vena cava wall 40, but do not penetrate the wall.

Further retraction of outer deployment member 44 causes complete exposure of the conical filtering structure 20 and the alignment ribs 8. As the alignment ribs are unsheathed, they expand outwardly and may contact wall 40 at alignment rib wall contact portion 10, depending on overall vessel diameter. Although not apparent in FIG. 7C due to the spatial orientation of the device 1, wall-engaging portions 15 of the primary filtering legs 13 and curved ends 16 of the secondary filter legs are in contact with the inner wall of the vessel. Although the filter 1 is fully engaged with the vessel wall 40 at this step, it has not yet been detached from the deployment device 25 and accordingly can still be repositioned if desired. To reposition, the inner deployment member 27 is retracted causing the filter to be drawn away from the vena cava wall 40 and into the outer deployment member 44. Alternatively, the outer deployment member 44 may be advanced causing the expanded filter 1 to collapse and be drawn into the deployment device 25. Once the filter 1 is collapsed within the outer deployment member 44, the deployment device 25 may be moved to the desired location and redeployed. Thus, in one novel aspect of the invention, the device and method of deployment provides for repositioning at any time prior to final detachment from the deployment device.

Figure 7D:
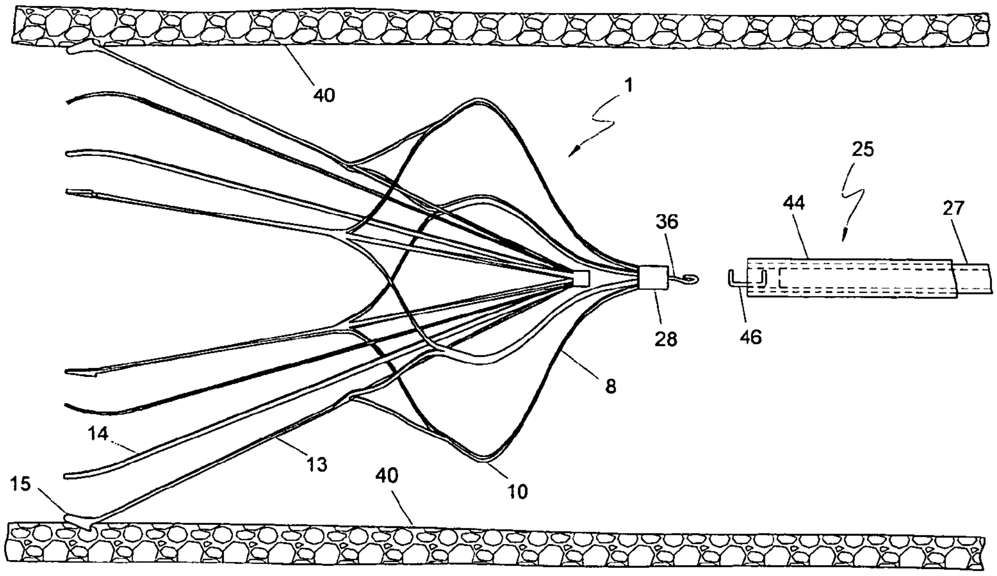

FIG. 7D depicts the filter 1 in its fully deployed configuration after detachment from the deployment device 25. To detach the filter 1 from the deployment device 25, the outer deployment member 44 is retracted to expose the retrieval hook subassembly 7 and the connector element 46 of the inner deployment member 27. Once unsheathed, the inner deployment member 27 may be rotated axially, causing the connector element 46 to disengage from the retrieval hook 36. This motion releases the filter from the deployment device 25. Once released, the deployment system 25 may be removed from the patient. Various other detachment mechanisms and release methods may be used to release the filter 1 from the deployment system 25. Once disconnected, the device 1 may be snared using a standard retrieval system if repositioning is still necessary.

The outer deployment member 25 thus control both the deployment and if desired the recapture of the filter 1 prior to full deployment. Advantageously, the filter may be repositioned before or after the wall-engaging portion 15 have engaged the vena cava wall 40 and after complete expansion of the filter 1 prior to disengagement from the deployment device 25. In addition, the deployment has the advantage of gradual and controlled deployment of the device by preventing the primary filtering legs 13, secondary filtering legs 14 and alignment ribs 8 from springing open suddenly, as is found with some prior art filter deployment systems.

FIG. 7A-7D depict a deployment of the filter 1 using a jugular vein approach. Although not shown, a femoral vein approach for deployment may sometimes be preferred. The vena cava filter of the current invention may be deployed from either approach. With the femoral approach, the filter 1 is positioned within the deployment device 25 in the opposite longitudinal orientation so that the hub end of the filter will be deployed first. Specifically, the alignment ribs 8 are deployed into the vessel first. The primary and secondary filter legs 13/14 are then deployed. The deployment device is then detached.

Thus, in a novel aspect of the current invention, a vena cava filter device is provided that is easy to deploy through a small delivery system using either a femoral or jugular approach and can be repositioned within the vessel after partial or even full deployment. Thus, the staged deployment design of this invention provides the user with not only a small, simple system that features controlled deployment from different approaches but provides the option of repositionability at each deployment step.

Figure 8A:
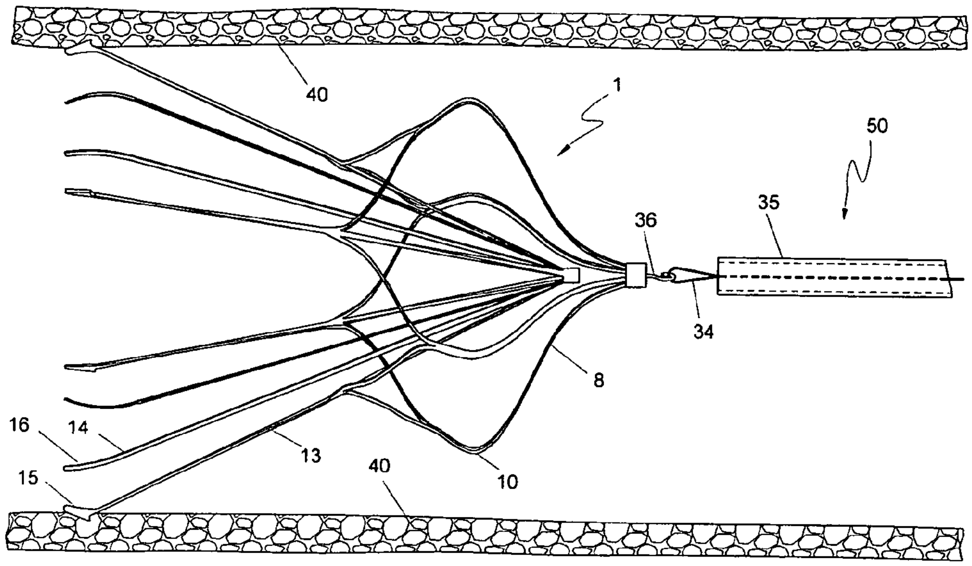
FIGS. 8A through 8D illustrate one exemplary method of retrieving the vena cava filter from the vessel.
Figure 8B:
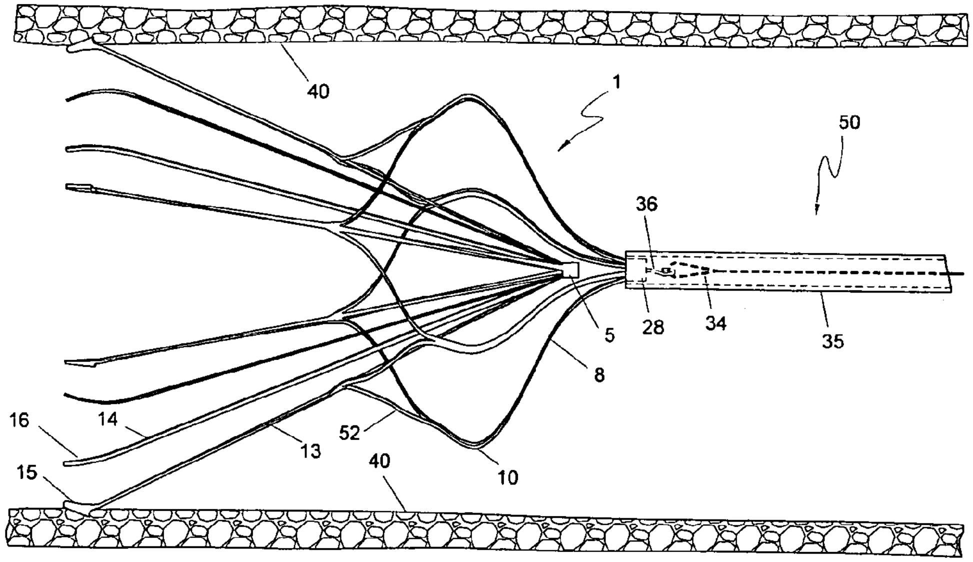

Methods of device retrieval will now be discussed with reference to FIG. 8A through 8D. FIG. 8A illustrates the first step in retrieval of the fully deployed filter 1 from within the vena cava. A standard sheath retrieval system 50 is comprised of a snare wire or loop 34 and a retrieval tube 35. In FIG. 8A, the snare loop 34 has been positioned around the retrieval hook 36 of the filter 1. Referring now to FIG. 8B, the retrieval tube 35 is advanced over the snare loop 34, the retrieval hook 36 and the outer tubular body hub 28 until these elements are totally enclosed within the lumen of the retrieval tube 35.

Figure 8C:
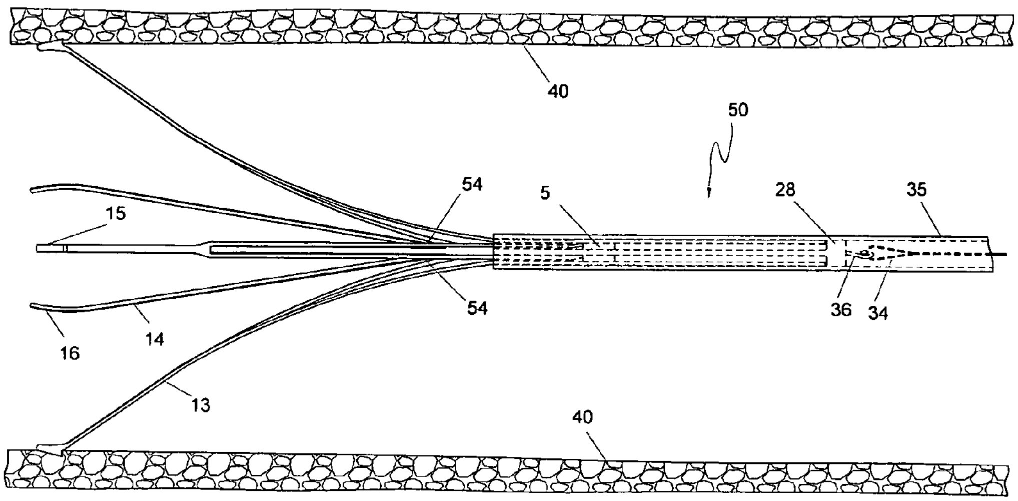

FIG. 8C depicts the retrieval step of collapsing the alignment structure 21. To activate the collapse of the alignment ribs 8, the retrieval tube is advanced further while holding the snare wire stationary causing the alignment ribs 8 of the filter 1 to be gradually drawn into the retrieval tube 35. Alternatively, the snare loop 34 may be retracted. As the retrieval tube is advanced further upstream, the alignment ribs 8 completely disengage from the vessel wall 40 (if they are in contact) and collapse toward the center of the vessel. A sharpened edge on the central-facing aspect of the wall-contacting portion 10 of alignment rib 8 will facilitate detachment without damaging the vessel wall, if endothelial overgrowth is present.

As the alignment ribs 8 collapse, the alignment rib branch points 54 are directed toward the center of the vessel, thereby forcing the secondary filtering legs 14, which are positioned within and between two adjacent alignment rib extensions 52, to also collapse inwardly. The continued inward force of the alignment rib branch points 54 causes the curved ends 16 of the secondary filtering legs 14 to gradually disengage from the vessel wall, as shown in FIG. 8C. Further collapse of the alignment ribs causes the primary legs 13 to begin arcing inward toward the longitudinal axis of the vessel. This directional movement allows for the atraumatic disengagement of the anchoring portion 15 from the vessel wall. Specifically, as the alignment ribs 8 completely collapse, the connecting point 24 of each rib and leg 13 is directed inwardly causing the barb 19 to pull out from the vessel wall at the same angle in which it was originally anchored. This method of disengagement is advantageous because the barbs pull out of the wall in a manner that creates only minimal vessel wall damage rather than slicing or tearing the neointimal layer.

Figure 8D:
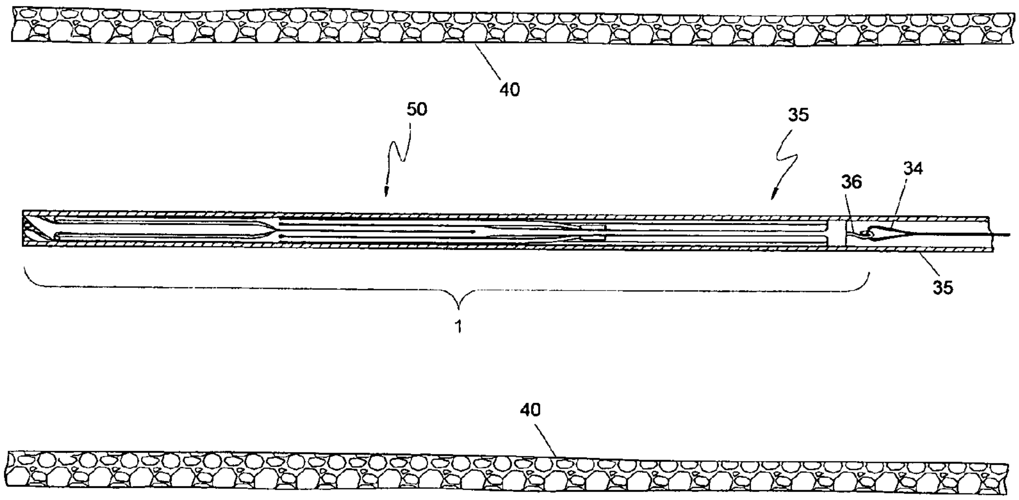

FIG. 8D depicts the collapsed filter device 1 totally enclosed within the retrieval sheath system 50. To complete the collapse the device 1, the retrieval tube 35 is advanced over the both secondary and primary filtering legs. Further advancement of the retrieval tube 35 causes complete collapse of the legs toward the central longitudinal axis. Alternatively, retraction of the snare loop 34 will cause collapse of the filter legs. Once the filter 1 is completed enclosed within the retrieval tube 35, the sheath is removed from the vein.

Thus the gradual collapse of the alignment structure provides for the sequential and symmetrical collapse of first the secondary legs and then the primary legs in a manner that avoids the common problems of vessel tearing, leg crossing and entanglement during retrieval. The interconnection between the alignment structure and the primary and secondary filtering legs ensures a smooth and symmetrical collapse of the legs. The design allows for the use of simple, non-proprietary retrieval device. In addition, the enclosed loop design of the alignment structure ensures that the snare wire 34 does not become entangled on the centering section as happens with prior art filters having free-ended centering legs that are prone to wire entanglement. The alignment structure design of the current invention also features the advantage of ensuring that the retrieval hook remains in the center of the vessel by the ribs, allowing for easy snaring of the device.

Figure 9:
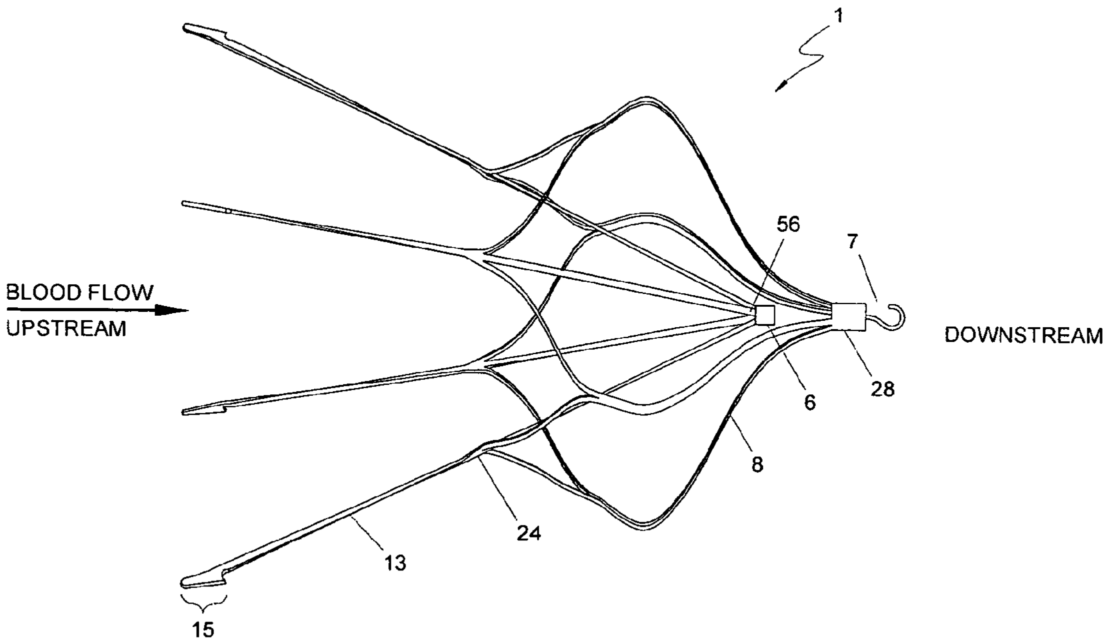
FIG. 9 is a plan view of an alternative embodiment of the vena cava filter device of the present invention in a deployed, expanded position.

The current invention is not limited to the specific embodiments disclosed herein. Other embodiments are possible. For example, FIG*s*. 9 and 10 illustrate two other embodiments of the blood clot filter 1 of the present invention wherein the elements having the same function as the previous embodiment are designated with the same reference numbers. FIG. 9 depicts an embodiment in which only the outer tubular body 3 and the retrieval hook subassembly 7 comprise the filter 1. The inner tubular body 17 with its secondary filtering legs 14 is not present in this embodiment. The filter 1 shown in FIG. 9 instead includes a ring connector element 6 which functions to draw free ends 56 of the filtering legs 13 together at the central axis to form a conical configuration. The connector ring 6 may be welded, press-fit or otherwise bonded to the downstream free ends 56 of the filtering legs 13, as previously described.

Figure 10:
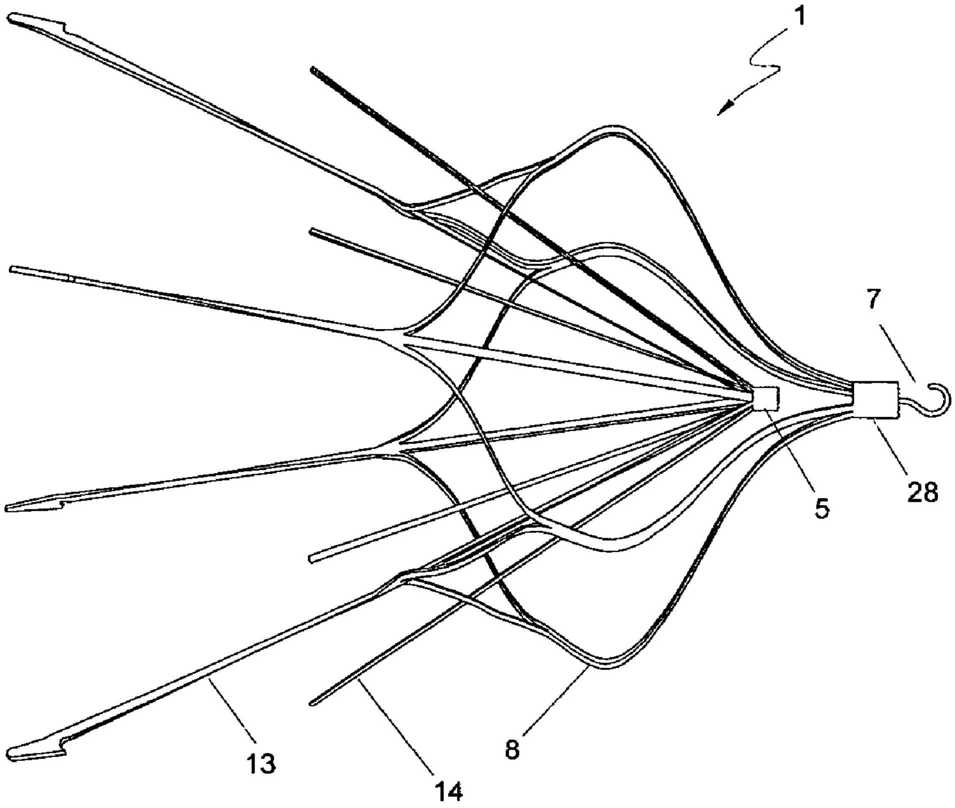
FIG. 10 is a plan view of another alternative embodiment of the vena cava filter device of the present invention in a deployed, expanded position.

FIG. 10 illustrates yet another embodiment in which the secondary filtering legs 14 are of a shortened length relative to the primary filtering legs 13. In this embodiment the shortened secondary filtering legs 14 provide both supplemental filtering capabilities and additional centering or alignment features. The leg ends 16 may contact the vessel wall 40 at a third plane between the primary legs and wall-contacting portion 10 of the alignment ribs 8. Although not shown, the leg ends 16 may be curved to prevent unintentional penetration of the vessel wall as previously described. Also although not shown, barbs may be configured on these legs to augment the filter securement in the vena cava. This design thus provides supplemental filtering, centering and anchoring capabilities through the use of a shortened inner tubular body 17 configuration.

Other configurations and methods of creating a retrievable vena cava filter are also possible. Modifications to the details illustrated in this disclosure, including filter and component shapes, numbers, barb designs, dimensions, materials, methods of construction and methods of use are within the scope of this invention. Accordingly, the scope of the invention is not limited to the foregoing specification, but instead is given by the appended claims along with their full range of equivalents.

What is claimed is:

1. A blood clot filter comprising:

a filter section including:

a filter hub;

a plurality of first filter legs having downstream ends connected to the filter hub and upstream ends, the first filter legs extending axially and radially outwardly from the filter hub; and an alignment section including:

an alignment hub;

a plurality of alignment ribs having downstream ends connected to the alignment hub and upstream ends connected to the first filter legs at points upstream of the filter hub, the alignment ribs extending from the alignment hub radially outwardly and then further extending radially inwardly; wherein the filter hub and the alignment hub are in longitudinal axis alignment.

2. The blood clot filter according to claim 1, wherein the alignment hub is spaced from and movable relative to the filter hub.

3. The blood clot filter according to claim 1, wherein:

each alignment rib includes first and second branches each having a downstream end and an upstream end;

wherein the downstream ends of the first and second branches of the each alignment rib are connected to each other, the upstream end of the first branch is connected to one of the first filter legs and the upstream end of the second branch is connected to an adjacent one of the first filter legs.

4. The blood clot filter according to claim 3, wherein each alignment rib further comprises an undivided portion having a downstream end connected to the alignment hub and an upstream end defining a junction point connected to the downstream ends of the first and second branches.

5. The blood clot filter according to claim 3, further comprising a plurality of second filter legs having downstream ends connected to the filter hub and being spaced from the first filter legs and positioned under the alignment ribs such that the alignment ribs limit radially outward movement of the second filter legs and during retrieval of the blood clot filter the alignment ribs push the second filter legs radially inward.

6. The blood clot filter according to claim 3, further comprising a plurality of second filter legs having downstream ends connected to the filter hub and being spaced from the first filter legs;

wherein the downstream ends of the first and second branches define a junction point; and wherein each second filter leg is substantially radially aligned with the junction point of an associated alignment rib relative to a longitudinal axis of the blood clot filter such that the alignment ribs limit radially outward movement of the second filter legs.

7. The blood clot filter according to claim 6, wherein the width of the second filter legs is less than the width of the first filter legs.

8. The blood clot filter according to claim 6, wherein the second filter legs are more flexible than the first filter legs.

9. The blood clot filter according to claim 1, wherein:

the plurality of first filter legs include at least four first filter legs spaced from each other; and the plurality of alignment ribs include at least four alignment ribs spaced from each other.

10. The blood clot filter according to claim 1, further comprising a plurality of second filter legs having downstream ends connected to the filter hub, and extending axially and radially outward in an upstream direction from the filter hub, the second filter legs being spaced from the first filter legs.

11. The blood clot filter according to claim 10, wherein the upstream ends of the second filter legs are curved to provide a less traumatic contact with the vessel wall.

12. The blood clot filter according to claim 1, further comprising a plurality of second filter legs having downstream ends connected to the filter hub and being spaced from the first filter legs, the length of the second filter legs being substantially the same as the first filter legs.

13. The blood clot filter according to claim 1, further comprising a plurality of second filter legs having downstream ends connected to the filter hub and being spaced from the first filter legs, wherein the second filter legs are unconnected to the alignment ribs.

14. The blood clot filter according to claim 1, wherein the upstream ends of the alignment ribs are connected to an intermediate zone of the first filter legs.

15. The blood clot filter according to claim 1, wherein:

the downstream ends of the first filter legs are free ends that are joined to the filter hub;

the downstream ends of the alignment ribs are integrally formed with the alignment hub; and the upstream ends of the alignment ribs are integrally formed with the first filter legs.

16. The blood clot filter according to claim 1, wherein:

the downstream ends of the alignment ribs are integrally formed with the alignment hub; and the upstream ends of the alignment ribs are integrally formed with the first filter legs.

17. The blood clot filter according to claim 1, wherein the alignment section and the first filter legs are made from a single tubular element.

18. The blood clot filter according to claim 1, further comprising:

a plurality of second filter legs having downstream ends connected to the filter hub and being spaced from the first filter legs;

wherein the alignment section and the first filter legs are made from a first single tubular element; and wherein the second filter legs and the filter hub are made from a second single tubular element.

19. The blood clot filter according to claim 1, further comprising a wall engaging portion at the upstream end of at least one of the first filter legs, the wall engaging portion having a barb generally pointed in the downstream direction.

20. The blood clot filter according to claim 19, wherein the wall engaging portion includes a generally smooth surface that rests against the vessel wall.

21. The blood clot filter according to claim 1, wherein an upstream portion of the first filter legs is rotated so as to facilitate anchoring of the barbs into the vessel wall.

22. The blood clot filter according to claim 1, further comprising a wall engaging portion at the upstream end of each first filter leg, the wall engaging portion having a foot that contacts the vessel wall, the foot including:

a major barb generally pointed in the downstream direction; and a plurality of minor barbs generally pointed in the upstream direction, the major and minor barbs being adapted to engage the vessel wall to reduce movement of the blood clot filter.

23. The blood clot filter according to claim 1, further comprising an engaging element positioned at the alignment hub and adapted to engage a retrieval mechanism to allow retrieval of the blood clot filter.

24. The blood clot filter according to claim 1, wherein the most radially outward portion of the alignment ribs defines a wall contact region adapted to contact a vessel wall to align the blood clot filter and an inward facing surface of the wall contact region includes a cutting edge to facilitate retrieval of the blood clot filter.

25. A blood clot filter capable of being retrieved, comprising:

a filter section including:

a filter hub;

a plurality of first filter legs having downstream ends connected to the filter hub and upstream ends, the first filter legs extending axially and radially outwardly from the filter hub; and an alignment section including:

an alignment hub movable relative to the filter hub and spaced from the filter hub;

a plurality of alignment ribs having downstream ends connected to the alignment hub and upstream ends connected to the first filter legs, the alignment ribs extending from the alignment hub radially outwardly and then further extending radially inwardly such that the most radially outward portion of the alignment ribs defines a wall contact region adapted to contact a vessel wall to align the blood clot filter;

wherein each alignment rib includes first and second branches each having a downstream end and an upstream end;

wherein the downstream ends of the first and second branches are connected to each other, the upstream end of the first branch is connected to one of the first filter legs and the upstream end of the second branch is connected to an adjacent one of the first filter legs.

26. The blood clot filter according to claim 25, wherein:

the alignment hub is spaced from and movable relative to the filter hub; and each alignment rib further includes an undivided portion having a downstream end connected to the alignment hub and an upstream end defining a junction point connected to the downstream ends of the first and second branches.

27. The blood clot filter according to claim 26, further comprising:

a plurality of second filter legs having downstream ends connected to the filter hub and being spaced from the first filter legs, the second filter legs being unconnected to the alignment ribs; and wherein each second filter leg is substantially radially aligned with the junction point of an associated alignment rib relative to a longitudinal axis of the blood clot filter such that the alignment ribs limit radially outward movement of the second filter legs.

28. The blood clot filter according to claim 25, wherein:

the downstream ends of the first filter legs are free ends that are joined to the filter hub;

the downstream ends of the alignment ribs are integrally formed with the alignment hub; and the upstream ends of the alignment ribs are integrally formed with the first filter legs.

29. The blood clot filter according to claim 25, further comprising a plurality of second filter legs having downstream ends connected to the filter hub and being spaced from the first filter legs;

wherein the alignment section and the first filter legs are made from a first single tubular element; and wherein the second filter legs and the filter hub are made from a second single tubular element.

30. The blood clot filter according to claim 25, further comprising a wall engaging portion at the upstream end of each first filter leg, the wall engaging portion having a barb generally pointed in the downstream direction.

31. The blood clot filter according to claim 25, further comprising a wall engaging portion at the upstream end of each first filter leg, the wall engaging portion having a foot that contacts the vessel wall, the foot having:

a major barb generally pointed in the downstream direction; and a plurality of minor barbs generally pointed in the upstream direction, the major and minor barbs being adapted to engage the vessel wall to reduce movement of the blood clot filter.

32. The blood clot filter according to claim 25, further comprising an engaging element positioned at the alignment hub and adapted to engage a retrieval mechanism to allow retrieval of the blood clot filter.

33. A method of retrieving a blood clot filter having:

a filter section including a filter hub, a plurality of first filter legs having downstream ends connected to the filter hub and upstream ends, and a plurality of second filter legs having downstream ends connected to the filter hub and being spaced from the first filter legs, an alignment section including an alignment hub and a plurality of alignment ribs having downstream ends connected to the alignment hub and upstream ends connected to the first filter legs, each alignment rib including first and second branches each having a downstream end and an upstream end, wherein the downstream ends of the first and second branches of the each alignment rib are connected to each other, the upstream end of the first branch is connected to one of the first filter legs and the upstream end of the second branch is connected to an adjacent one of the first filter legs, the method comprising:

capturing the alignment hub;

moving a sheath over the alignment ribs so as to cause the second filter legs to be pushed radially inwardly by the alignment ribs; and further moving the sheath over the first filter legs to cause the first filter legs to be pushed inwardly.

34. The method according to claim 33 wherein the step of capturing includes:

engaging an engaging element disposed at the alignment hub; and placing the sheath over the alignment hub while the engaging element is engaged.

* * * * *

UNITED STATES PATENT AND TRADEMARK OFFICE

CERTIFICATE OF CORRECTION

PATENT NO. : 7,279,000 B2 
APPLICATION NO. : 11/165675
DATED : October 9, 2007
INVENTOR(S) : William A. Cartier et al.

It is certified that error appears in the above-identified patent and that said Letters Patent is hereby corrected as shown below:

TITLE PAGE:

[73] Assignee: AngioDynamics, Inc, Queensbury, NY (US)

Should be inserted after Item (76)

Signed and Sealed this

Eleventh Day of December, 2007

JON W. DUDAS
*Director of the United States Patent and Trademark Office*